United States Patent
Azuma et al.

(10) Patent No.: US 8,328,723 B2
(45) Date of Patent: Dec. 11, 2012

(54) ULTRASOUND DIAGNOSIS APPARATUS

(75) Inventors: Takashi Azuma, Kodaira (JP); Shinichiro Umemura, Sendai (JP)

(73) Assignee: Hitachi Medical Corporation, Tokyo (JP)

( * ) Notice: Subject to any disclaimer, the term of this patent is extended or adjusted under 35 U.S.C. 154(b) by 956 days.

(21) Appl. No.: 11/996,511

(22) PCT Filed: Jun. 20, 2006

(86) PCT No.: PCT/JP2006/312277
§ 371 (c)(1),
(2), (4) Date: Feb. 13, 2009

(87) PCT Pub. No.: WO2007/032134
PCT Pub. Date: Mar. 22, 2007

(65) Prior Publication Data
US 2009/0270730 A1    Oct. 29, 2009

(30) Foreign Application Priority Data
Sep. 14, 2005  (JP) .................................. 2005-267312

(51) Int. Cl.
*A61B 8/13* (2006.01)
(52) U.S. Cl. ..................... 600/439; 600/443; 600/437
(58) Field of Classification Search .................. None
See application file for complete search history.

(56) References Cited

U.S. PATENT DOCUMENTS

| | | | | |
|---|---|---|---|---|
| 4,781,200 A | * | 11/1988 | Baker | 600/483 |
| 5,860,931 A | * | 1/1999 | Chandler | 600/458 |
| 6,488,626 B1 | | 12/2002 | Lizzi et al. | |

FOREIGN PATENT DOCUMENTS

JP     2003-210456     7/2003

OTHER PUBLICATIONS

M.M Doyley, I.C. Bamber, L.Rivens, N.L. Bush, and G.R. ter Harr, "Elasotgraphic Imaging of thermally ablated tissue in vitro", 1999 IEEE Ultrasonics Symposium p. 1631.

* cited by examiner

*Primary Examiner* — Long V. Le
*Assistant Examiner* — Farshad Negarestan
(74) *Attorney, Agent, or Firm* — Antonelli, Terry, Stout & Kraus, LLP.

(57) ABSTRACT

An ultrasound diagnosis apparatus includes an ultrasound probe 1, in which a plurality of transducer elements are arrayed and which converges and radiates an ultrasound on a patient and detects a reflection wave thereof, and images a tomogram of the patient, using the reflection wave, wherein an expansion detector 22 operates a difference between a radial component of a therapeutic converging beam of a movement amount of each part, and an integral amount integrated from the radial component, and extracts a tissue expansion generated at a part of the patient from the tomogram, and wherein the movement amount is calculated by performing a pattern matching between tomograms imaged with different frames.

12 Claims, 14 Drawing Sheets

Treated Region

M Mode Image

Before Radiation

During Radiation

B Mode Image      Image of Tissue Expansion

Template of Tissue Expansion

ULTRASOUND DIAGNOSIS APPARATUS

TECHNICAL FIELD

The present invention relates to an ultrasound diagnosis apparatus for using an ultrasound probe and diagnosing a patient.

BACKGROUND ART

Heating coagulation therapies are methods of thermally treating a malignant tumor such as a prostate cancer, a liver cancer, and a breast cancer; and a diseased part such as a uterine myoma and a prostrate hypertrophy by radiating a strong converging ultrasound beam radiation or an electromagnetic wave such as an RF (Radio Frequency) beam and a microbeam. These treatment methods enable a therapy without an incision of a body surface, and therefore, their application to clinical practice is enlarging as a minimally invasive treatment method.

Furthermore, an ultrasound imaging method makes it possible to observe a tomogram of a living body in real time; however, it images only a region of not less than a boiling point, and it is difficult to image a protein denaturation region of 60 Celsius degrees to less than 100 Celsius degrees generated by the heating coagulation therapies.

In order to solve the problem, there are disclosed an elastic modulus imaging method of using a pressurizing method and a radiation region imaging method of using a radiation force of a strong converging ultrasound beam.

The elastic modulus imaging method is a method of pressurizing a body surface from outside while imaging an ultrasound tomogram, estimating a displacement degree according to a correlation between received signals of different time phases, and presuming that a region where the displacement is large is a soft region and that a region where the displacement is small is a hard region (non patent document 1). Furthermore, with respect to the radiation region imaging method of using the radiation force, if a temperature of a radiation region rises by an ultrasound treatment, an absorption coefficient of an ultrasound of the region selectively becomes large compared to a surrounding tissue; therefore, the radiation force selectively acts only on the region of a temperature rise, and the region is moved and displaced toward a direction away from a therapeutic transducer; therefore, the radiation region imaging method is a method of detecting the displacement region (patent document 1).

Non patent document 1: 1999 IEEE ULTRASONICS SYMPOSIUM p. 1631 Elasotgraphic Imaging of thermally ablated tissue in vitro M. M Doyley, I. C. Bamber, L Rivens, N. L. Bush, and G. R. ter Harr Patent document 1: Specification of U.S. Pat. No. 6,488,626

DISCLOSURE OF THE INVENTION

When an elastic modulus imaging method is used in monitoring a minimally invasive treatment, it is difficult to apply the method to a region far from a body surface which a force does not cover well because of a necessity of a pressurization from outside. On one hand, in an imaging method using the radiation force, when a patient is moving by a tissue motion such as a respiration, it is difficult to distinguish between a displacement caused by the tissue motion and that caused by the radiation force.

The present invention is made in view of the above mentioned situation, and an objective of the invention is to provide an ultrasound diagnosis apparatus that can detect a tissue expansion caused by a thermal denaturation generated at a region remote from a body surface of a patient.

The ultrasound diagnosis apparatus of the present invention comprises an ultrasound probe, in which a plurality of transducer elements are arrayed and which converges and radiates an ultrasound on a patient and detects a reflection wave thereof, and images a tomogram of the patient, using the reflection wave; and the apparatus extracts from the tomogram a tissue expansion generated on a part of the patient. The tissue expansion is generated by converging and radiating on a part of the patient a therapeutic converging beam that is any one of the ultrasound, another ultrasound, an electromagnetic wave, and their combination; and is extracted by operating a difference between a radial component of the therapeutic converging beam of a displacement of each part, which is obtained by a pattern matching between the tomogram imaged with one frame and the tomogram imaged with another frame, and an integral amount integrated from the radial component.

Thus it is possible to extract a tissue expansion caused by a thermal denaturation generated on a part of a patient by a radiation of a therapeutic converging beam.

According to the present invention, it is possible to extract a tissue expansion caused by a thermal denaturation generated on a region remote from a body surface of a patient.

BEST MODE(S) FOR CARRYING OUT THE INVENTION

First Embodiment

Figure 1:
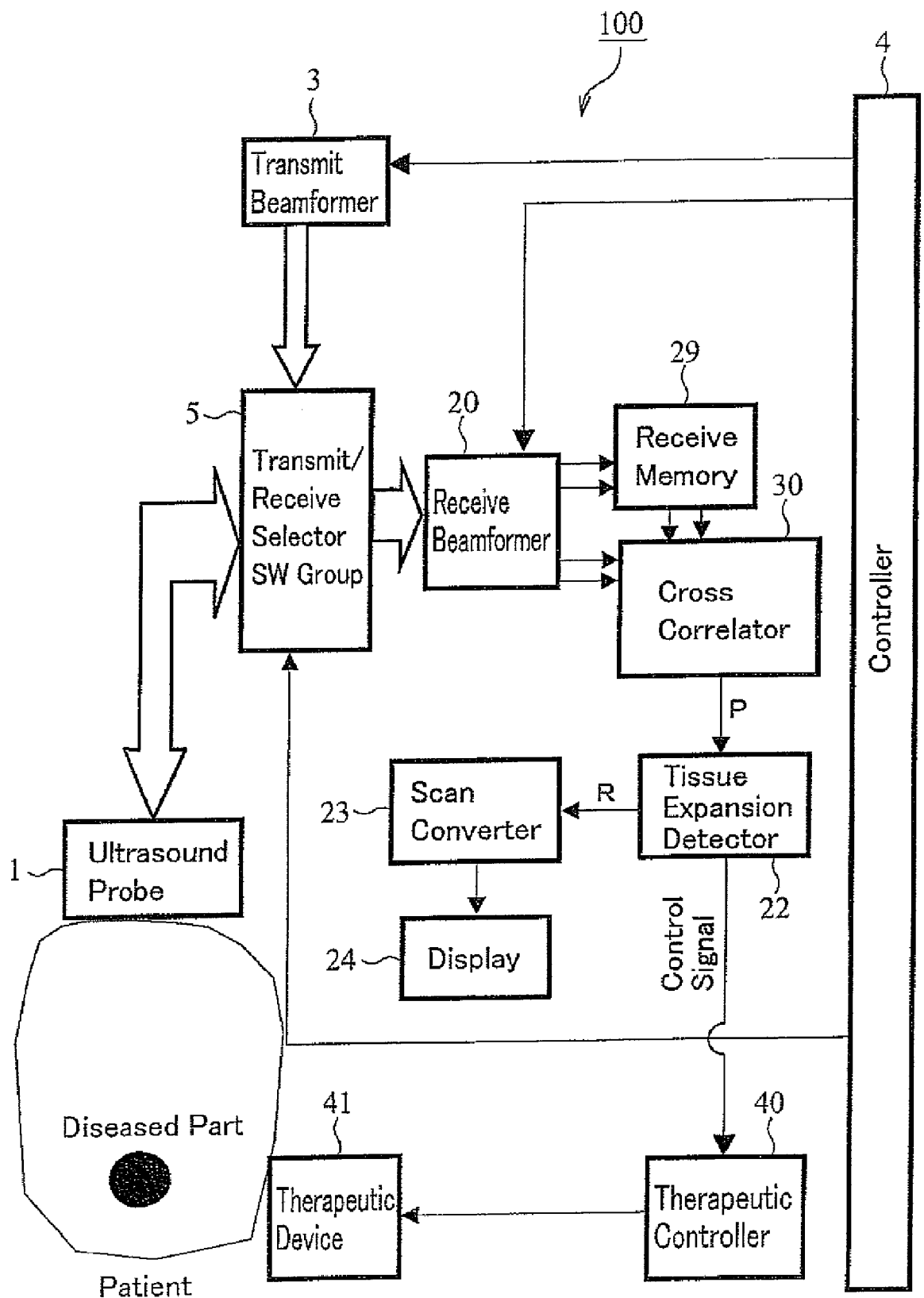
FIG. 1 is a configuration drawing of an ultrasound diagnosis apparatus of an embodiment of the present invention.

FIG. 1 is a configuration drawing of an ultrasound diagnosis apparatus of an embodiment of the present invention.

An ultrasound diagnosis apparatus 100 includes an ultrasound probe 1 for converging and radiating an ultrasound on a diseased part of a patient and performing a heating coagulation therapy; and an ultrasound imaging device for using an ultrasound echo and imaging the patient, wherein the ultrasound probe 1 consists of a therapeutic device 41 and a therapeutic controller 40. In addition, as the therapeutic device 41, it is also possible to use an RF therapeutic probe for radiating an electromagnetic wave such as an RF beam and a microbeam. In addition, the ultrasound imaging device extracts a change of an acoustic impedance of a patient as an differentiation image, and comprises: the ultrasound probe 1; a transmit/receive selector SW (Switch) group 5; a transmit beamformer 3; a receive beamformer 20; a beam receiving memory 29; a cross correlator 30 of an operation means for performing a pattern matching; an expansion detector 22; a scan converter 23; a display 24; and a controller 4.

Figure 2A:
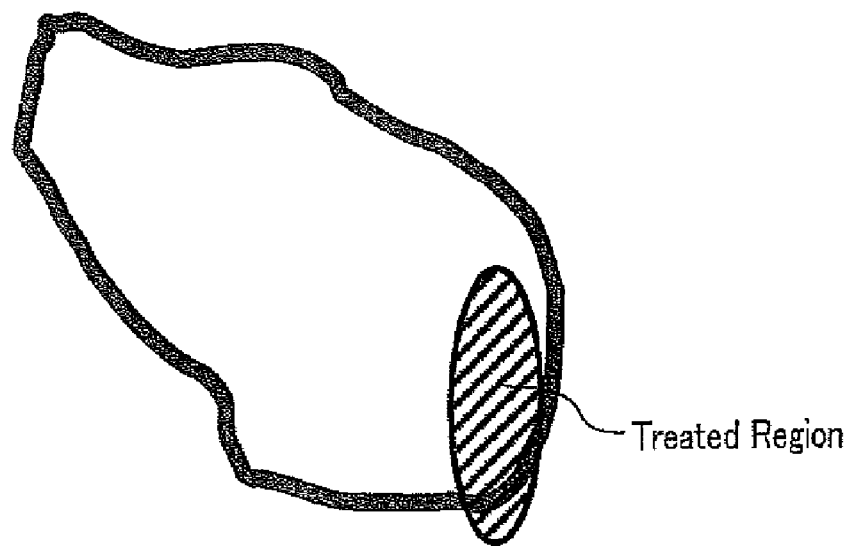
FIGS. 2A and 2B are illustration drawings of a treatment method in a heating coagulation therapy.
Figure 2B:
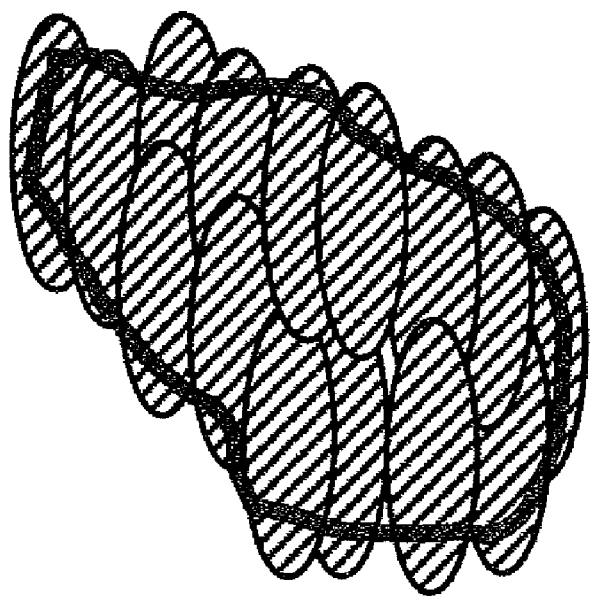

Here, heating coagulation therapies are methods of thermally treating a malignant tumor such as a prostrate cancer, a liver cancer, and a breast cancer; and a diseased part such as a uterine myoma and a prostrate hypertrophy by radiating a strong converging ultrasound beam radiation or an electromagnetic wave such as an RF (Radio Frequency) beam and a microbeam. These treatment methods enable a therapy without an incision of a body surface, and therefore, their application to clinical practice is enlarging as a minimally invasive treatment method. Because all of a radiation region is not always treated by one time radiation, normally as shown in FIGS. 2A and 2B, a strong converging ultrasound beam is radiated by a plurality of times and all of the radiation region is treated without a failure. Whereas, a cancer indicates a complicated form; because a form of a region treatable by the heating coagulation therapy is geometrically constant, the form by one time therapy is as shown in FIG. 2A. Although it is possible to widen a radiation region to an extent that all of the radiation region is covered by one time therapy, it is not preferable because in that case there is a possibility that a normal tissue in the vicinity of the radiation region is also widely damaged. Therefore, as shown in FIG. 2B, the heating coagulation therapy is performed by radiating the strong converging ultrasound beam by the therapeutic device 41, overlapping a part of the radiation region, and covering all of the radiation region. Accordingly, it is indispensable in the heating coagulation therapy to grasp an accurate form of a radiation region for every radiation. If a part of a cancer remains untreated, finally the cancer propagates again therefrom; therefore, it is important to determine whether or not a therapeutic target region is completely treated, and additionally important to monitor a radiation region of each radiation and to be able to present the radiation region to a surgeon, also from a viewpoint of suppressing damage at minimum to a surrounding normal tissue as a minimally invasive treatment.

The ultrasound probe 1 consists of a plurality of transducer elements (piezoelectric bodies) transmits an ultrasound beam to a patient of an inspection object and receives an echo from the patient. The transmit beamformer 3 generates under control of the controller 4 a transmit signal of a delay time matched with a transmit focus depending on a transmitted signal. Furthermore, the transmit/receive selector SW group 5 divides a plurality of transducer elements. For example, the transmit/receive selector SW group 5 controls a focus position of an ultrasound in a patient by dividing a plurality of transducer elements like a concentric circle and by using a Fresnel ring bundle method that applies a same phase signal to the transducer elements divided into a same area.

An ultrasound signal, which is reflected or scattered in a patient and returned to the ultrasound probe 1, is converted to an electric signal by the probe 1, and is again transmitted to the receive beamformer 20 through the transmit/receive selector SW group 5. Here, the receive beamformer 20 performs a dynamic focus of adjusting a delay time, depending on a receiving timing, under the control of the controller 4. The receive beamformer 20 displaces a signal which each element of an array receives by a time depending on a difference between a distance of a desired position and that of each element position, and adds the signal, and thereby, reinforces a signal from the desired position. In addition, it becomes possible to take an image at a high speed by dividing the element and simultaneously forming a plurality of received beams.

An output of the receive beamformer 20 is stored in the receive memory 29, a pattern matching between receive beamformer output data with respect to a same scan line is performed at different times by the cross correlator 30, and a spatial distribution of a displacement of a patient is obtained. As a pattern matching, there exist a method of making a movement amount, where a cross correlation function becomes maximum, a displacement (deformation amount); and a method of making a movement amount, where a square sum of a difference between two functions becomes minimum, a displacement. By scanning an ultrasound pulse over all of an imaging region, a tomogram can be obtained. Such a pulse echo method of an ultrasound receives an echo from an interface where an acoustic impedance changes in a patient, and detects a received signal as an envelope, and thereby, makes an image of a tomogram. An ultrasound tomogram is in real time; a device therefore is small and movable, and therefore, is widely being utilized also as a monitoring device of a heating coagulation therapy described below.

Figure 3:
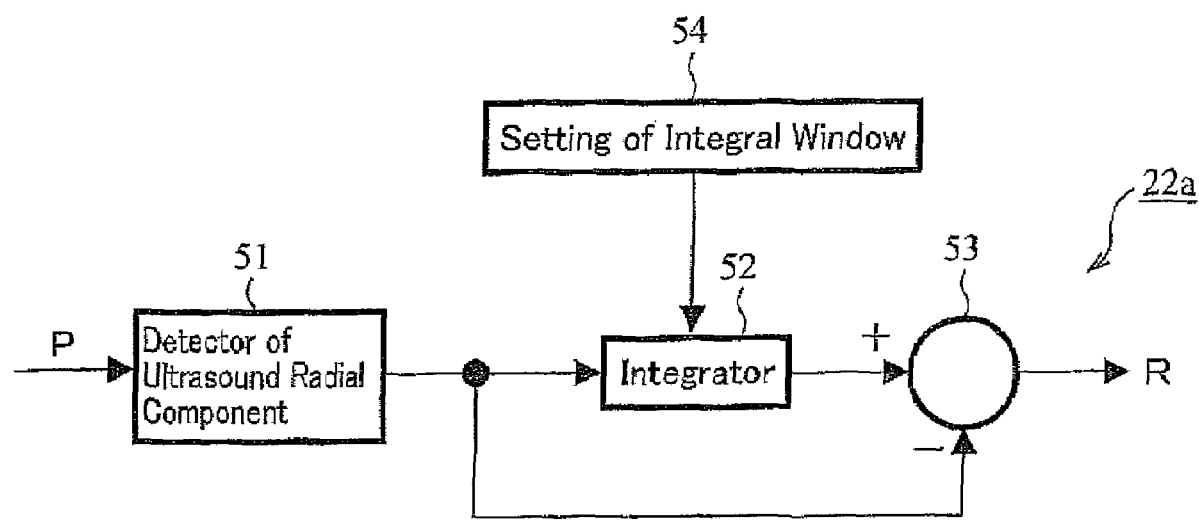
FIG. 3 is a configuration drawing of a tissue expansion detector of a first embodiment of the present invention.

An inner configuration of the expansion detector 22 is specifically described in FIG. 3, and FIGS. 9A and 9B described later. In FIG. 3, an expansion detector 22a corresponding to the expansion detector 22 comprises a detector 51 of an ultrasound radial component, an integrator 52, a subtracter 53, and a setting 54 of an integral window. A displacement P from the cross correlator 30 is input to the detector 51 of an ultrasound radial component, and a radial component of a therapeutic ultrasound is calculated. This radial component and a radial component integrated by the integrator 52 are subtracted by the subtracter 53, and input to a scan converter 23 as a tissue expansion component R.

Thus by performing an integration operation of a displacement (deformation amount) in a radial direction of a therapeutic ultrasound, a symmetric component of motions to a near side and a far side is suppressed and one-direction motions of such a radiation force and a tissue motion can be detected. By subtracting the one-direction motions from a whole signal, a true tissue expansion component is detected.

The setting 54 of an integral window sets an integral range of the integrator 52, and it is necessary to set the integral range wider than an estimation range of a tissue expansion.

Figure 4A:
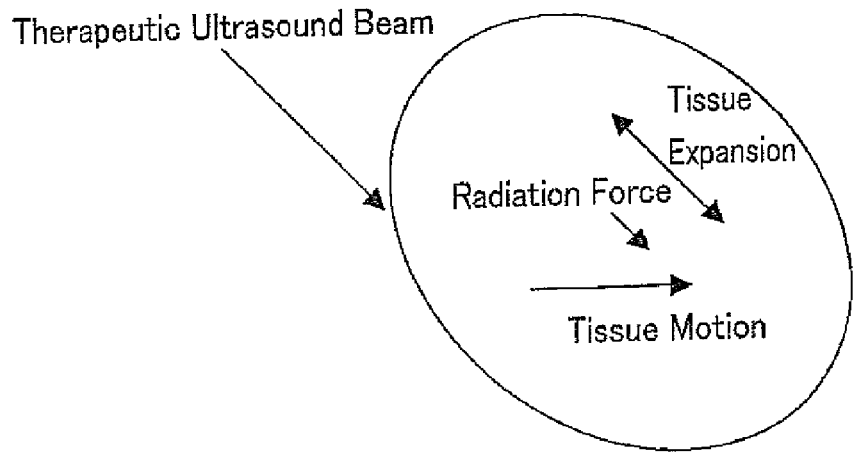
FIGS. 4A, 4B, and 4C are drawings explaining a method of distinguishing a tissue expansion from a radiation force and a tissue motion.
Figure 4B:
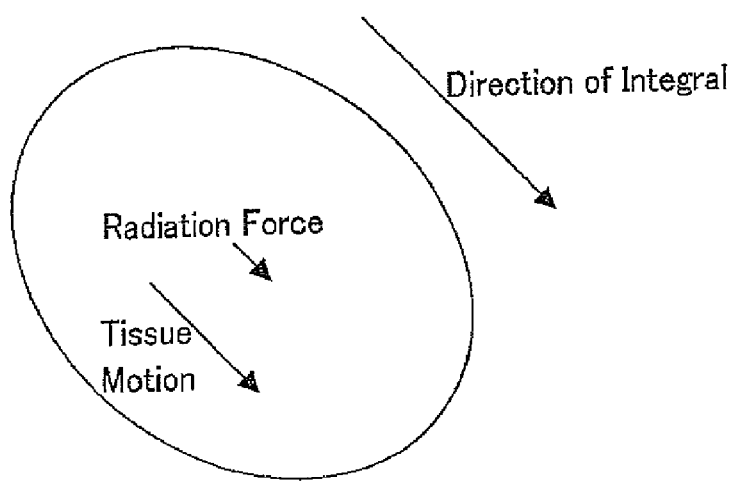
Figure 4C:
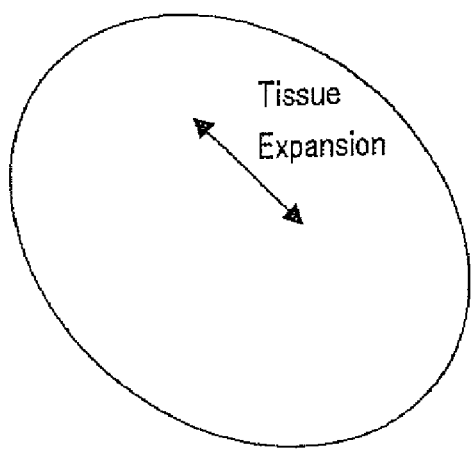

Next will be considered a case of a tissue expansion, a radiation force, and a tissue motion being generated in a diseased part where a therapeutic ultrasound beam is converged and radiated, with reference to FIGS. 4A, 4B, and 4C. In FIG. 4A, the tissue motion results from a normal respiration and a heart motion, moves with a whole internal organ, and therefore, is assumed to be a motion in one direction. Although a motion resulting from a heart is more complicated in a moving way than that resulting from a respiration, the motion resulting from the heart can be assumed to be a motion in one direction because it moves so as to be propagated, making the heart an origin thereof. Using this matter, it is possible to detect a displacement caused by a tissue expansion while removing a displacement caused by a tissue motion. If each displacement component of FIG. 4A is integrated in a propagation direction of the therapeutic ultrasound beam, only the tissue expansion component is obliterated as shown in FIG. 4B. Then if a difference between FIG. 4A and FIG. 4B is taken, only the tissue expansion component is extracted as shown in FIG. 4C.

Figure 5:
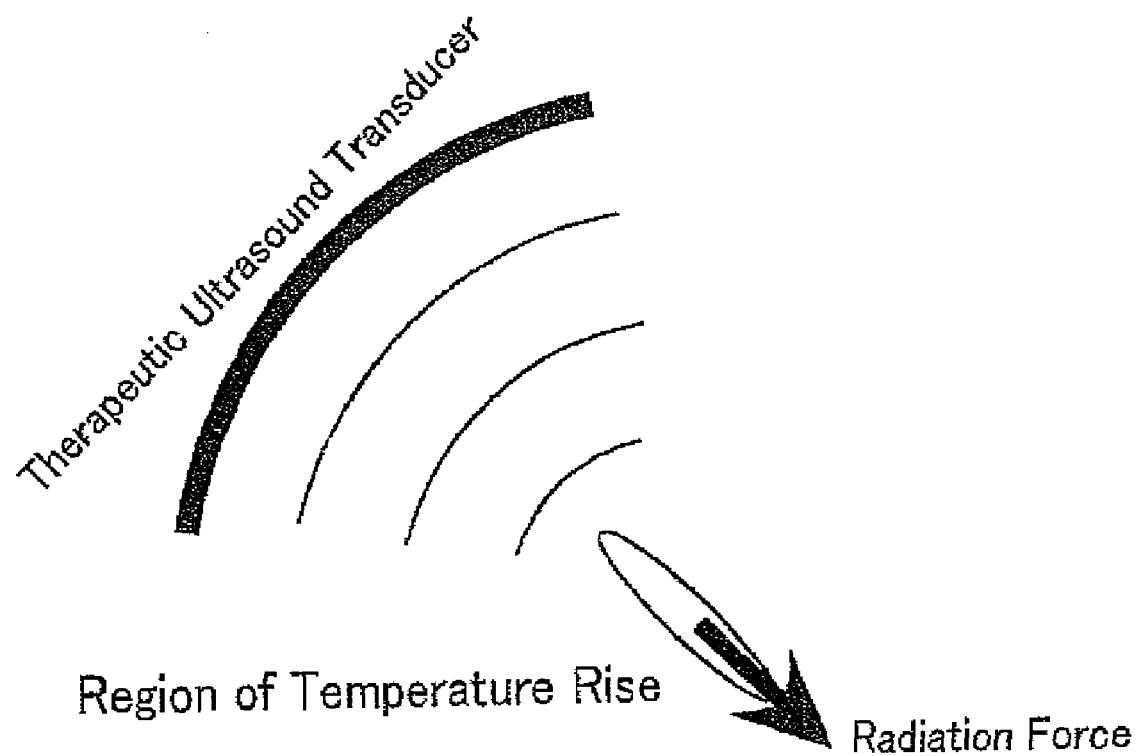
FIG. 5 is an illustration drawing of a monitoring method of using a radiation force.

Here will be described a radiation force with reference to FIG. 5. The therapeutic device 41 of a therapeutic ultrasound transducer converges and radiates an ultrasound toward a diseased part from a body surface. Thus an ultrasound vibration is transferred to a patient, and the diseased part is elastically displaced in the direction of the therapeutic ultrasound beam. A pressure that becomes a cause of the elastic displacement is the radiation force, and a region of a temperature rise is generated in the vicinity of a focus point by the vibration.

In the embodiment, by the expansion detector 22 is distinguished a case of being displaced so as to be symmetrically propagated to front and back of a radial component of a sound, wherein a displacement of a patient is related to a tissue expansion; and a case of being displaced only in one direction caused by a tissue motion or a radiation force.

The scan converter 23 converts an image detected by the expansion detector 22 to a two-dimensional image or a three-dimensional image. The display 24 makes a CRT or a liquid crystal a base, and displays the two-dimensional image or the three-dimensional image converted by the scan converter 23. In addition, in a conventional elastic modulus imaging and a strain image using a radiation force, the displacement spatial distribution is displayed through the scan converter 23 on the display 24 independently or with being superimposed on a B (Brightness) mode image.

This image display is configured to be able to display any of a conventional B mode image, a tissue expansion extraction image, and these by being overlapped. In order to display them by being superimposed, such a method is assumed that displays a tissue expansion with a color in contrast to a B mode image of white and black. Furthermore, it is possible to display a motion positioned at a near side of a transducer and a motion toward a far side with different color codes, for example, blue for the near side and red for the far side, and also to display only an absolute value of the motion. Although a displacement caused by a tissue expansion is distinguished from another displacement, it is useful to plainly present a tissue expansion component from a viewpoint of providing many pieces of information by a surgeon by displaying blue for the near side and red for the far side.

In an ultrasound tomogram, sampling minuteness is largely different between a propagation direction (hereinafter referred to as a radial direction) of an imaging ultrasound beam and a direction orthogonal thereto (hereinafter referred to as a azimuthal direction). This is because: the sampling minuteness in the radial direction is typically the extent of 30 μm since a sampling thereof is performed for a wavelength of an ultrasound; whereas, the sampling minuteness in the azimuthal direction is a few 100 μm since a sampling thereof is performed for a beam width of around 1 mm width. Because a point response function of an ultrasound beam is thus widened in the azimuthal direction, the sampling is taken minutely in the radial direction and roughly in the azimuthal direction; thereby, the sampling is performed neither too much nor too few, and a balance of a tradeoff between a spatial resolution and a time resolution is taken. Therefore, because a displacement detection accuracy is also largely different between the radial direction and the azimuthal direction, it normally suffices to match an direction of integral with the radial direction. In order to maximally take advantage of a ratio of a signal to a noise in this method, it is also preferable to match a transmit direction of a converging ultrasound beam with a propagation direction of an imaging ultrasound beam as much as possible.

Figure 6:
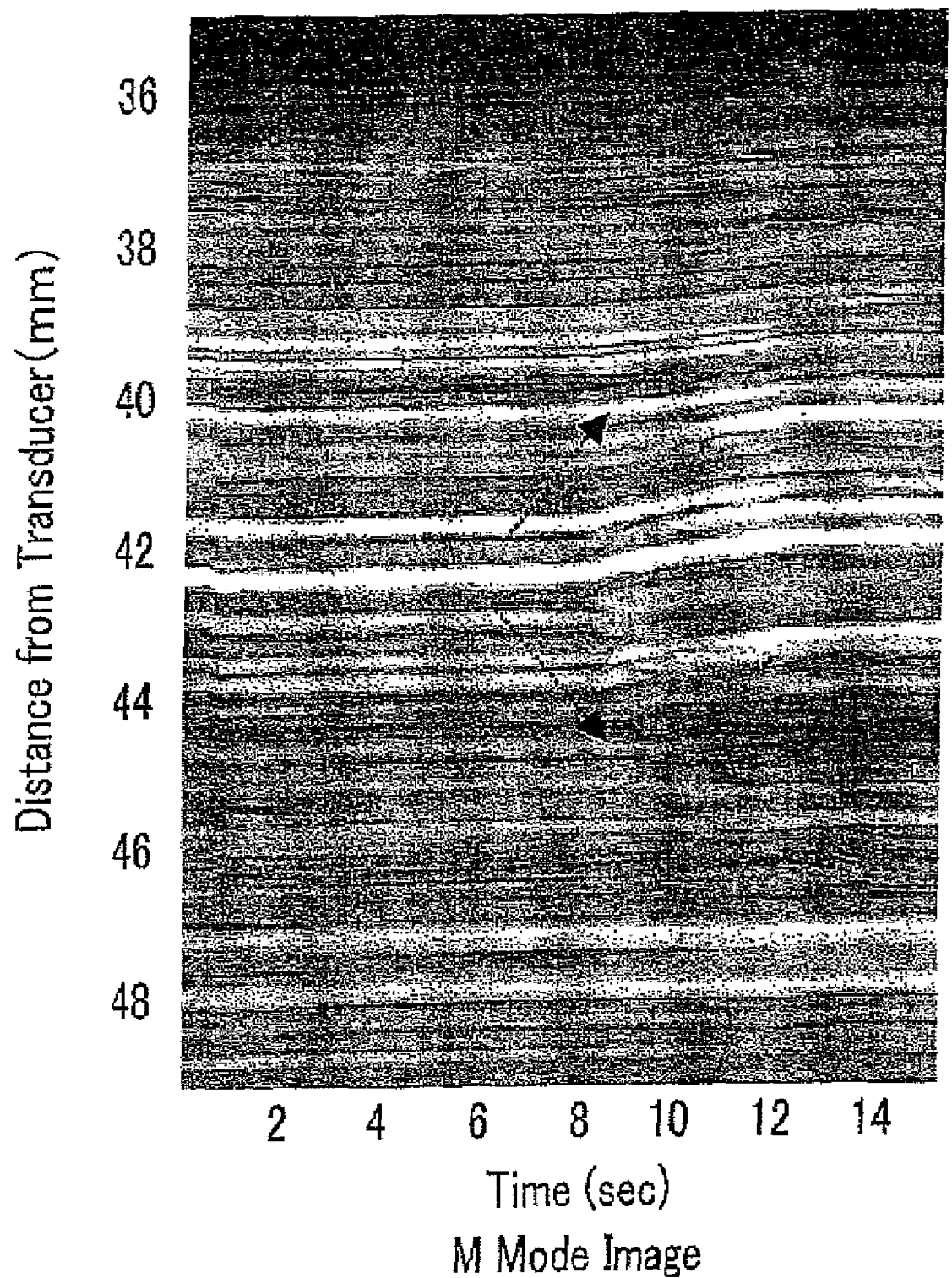
FIG. 6 is an M mode image where a tissue expansion is captured by a method of the embodiment.

FIG. 6 shows an imaging result called an M (Motion) mode, wherein a time [second] is shown in a horizontal axis and a distance [mm] in a radial direction is shown in a vertical axis. The M mode is a mode for imaging a motion, and the image, wherein a scan line is fixed in an azimuthal direction, a depth is shown in the vertical axis, and a time is shown in the horizontal axis. If a therapeutic ultrasound beam is made ON at a time of about one second in the time-axis, a living body tissue uniformly moves in the radial direction of the ultrasound because of a radiation force. Although any change cannot be seen for a while then, the living body tissue symmetrically moves in the radial direction, making a diseased part around a depth of 43 mm from about 8 seconds of the time axis. This is a typical displacement caused by a tissue expansion.

Figure 7:
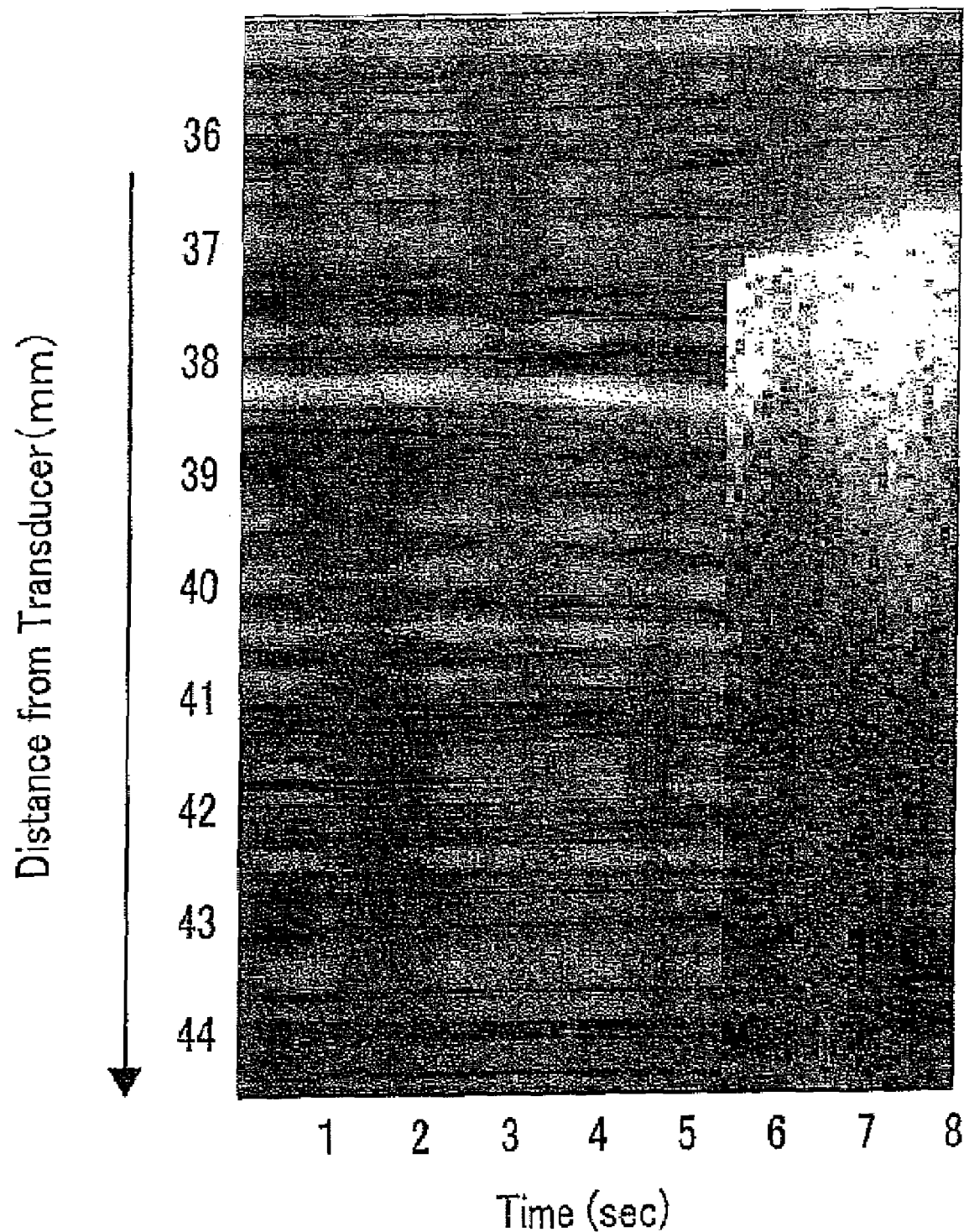
FIG. 7 is an M mode image where a radiation force is captured.

On one hand, FIG. 7 shows an M mode image in a system where a radiation force has become predominant as a result of having displaced a position of a maximum pressure and a position of a maximum temperature rise. When the radiation force is predominant, a motion cannot have been detected only in a direction away from the therapeutic device 41 of a transducer; whereas, it turns out well in FIG. 6 that the tissue expansion can have been detected.

Figure 8A:
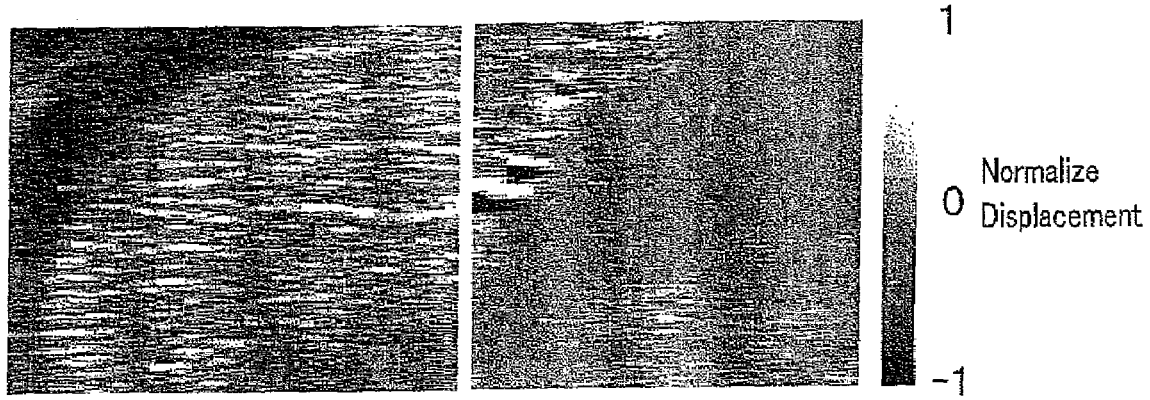
FIGS. 8A and 8B are B mode images and images of tissue expansions compared between before and during a radiation, respectively.
Figure 8B:
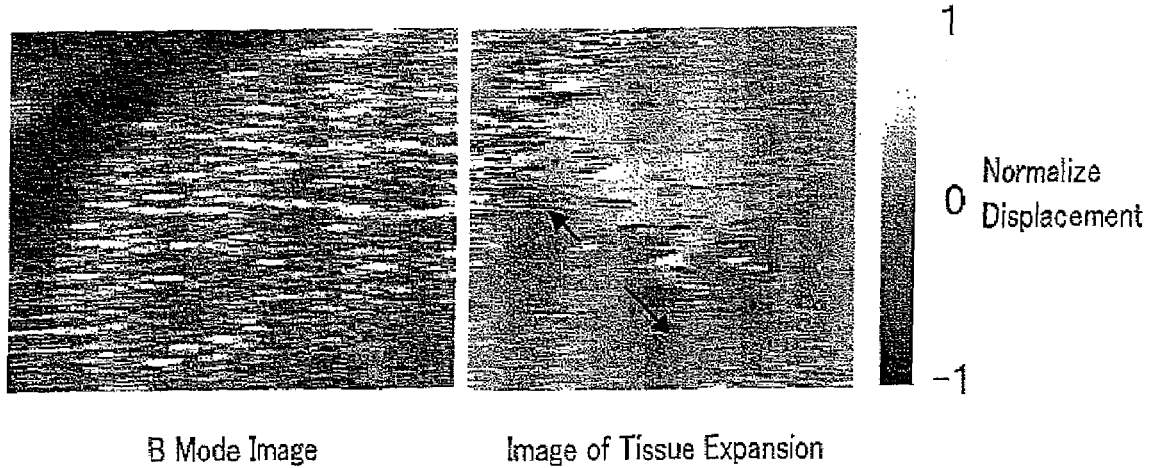

Although in FIG. 6 the tissue expansion is indicated according to a time change of certain one-dimensional data, in FIGS. 8A and 8B a time is selected and a tissue expansion is indicated as a two-dimensional tomogram. In FIG. 8A a tomogram at a time of one second is indicated, and in FIG. 8B a tomogram at a time of 10 seconds is indicated; each left figure is a B mode image, and each right figure is an image of a tissue expansion. In the B mode the tissue expansion not detected can be distinctly observed during a radiation in the right figure. In addition, on the right of each image of the tissue expansion is indicated a scale that indicates a normalize displacement from 1 to −1 with shading.

In order to enhance an estimation accuracy of the tissue expansion, it is also effective not to restrict imaging signals, of which a cross correlation is taken, to two. By taking a cross correlation between not less than three signals and looking into a temporal change of the cross correlation, it becomes possible to use a temporal average value of a cross correlation value and make an inspection result have a stability; on the contrary, by looking into a temporal change component, it becomes possible to detect an acceleration rate of the tissue expansion.

In addition, if in the embodiment the expansion detector 22 detects a tissue expansion, the unit 22 is adapted to transmit a control signal to the therapeutic controller 40 so that the therapy is stopped. Namely, if an area of an existing radiation region caused by a tissue expansion exceeds a definite value, the therapy is adapted to be stopped, or to be finished when a definite time elapses after the detection of the tissue expansion. Particularly, when a strong converging ultrasound beam is used, it is adapted to generate a heating coagulation region by a radiation normally for a few seconds in order to eliminate a disturbance factor of a heat conduction of a living body. If boiling is caused by the ultrasound radiation in the case of the heating coagulation, a bubble is generated, becomes a scattering body of the ultrasound, and in some cases an ultrasound intensity becomes high in a region other than therapy intended region; therefore, when a tissue expansion is detected, it is preferable to immediately stop the therapy.

According to the embodiment thus described, it is possible to detect a displacement caused by a tissue expansion accompanied by a protein thermal denaturation in a radiation region of a heating coagulation therapy by a correlation between ultrasound signals before and after the tissue expansion. Namely, also in a living-body deep position where pressurization is difficult, it becomes possible to monitor a heating coagulation by monitoring a tissue expansion accompanied by the thermal denaturation, without radiating a therapeutic strong ultrasound beam. Furthermore, it is possible to make small an influence of such a thing like a tissue motion that becomes a disturbance factor of monitoring.

Second Embodiment

Although in the first embodiment the tissue expansion is detected by calculating the ultrasound radial component of a displacement and by obtaining a difference between the ultrasound radial component and an integral amount thereof, it is also possible to detect the tissue expansion by operating a cross correlation between a displacement and a template of a tissue expansion.

Figure 9A:
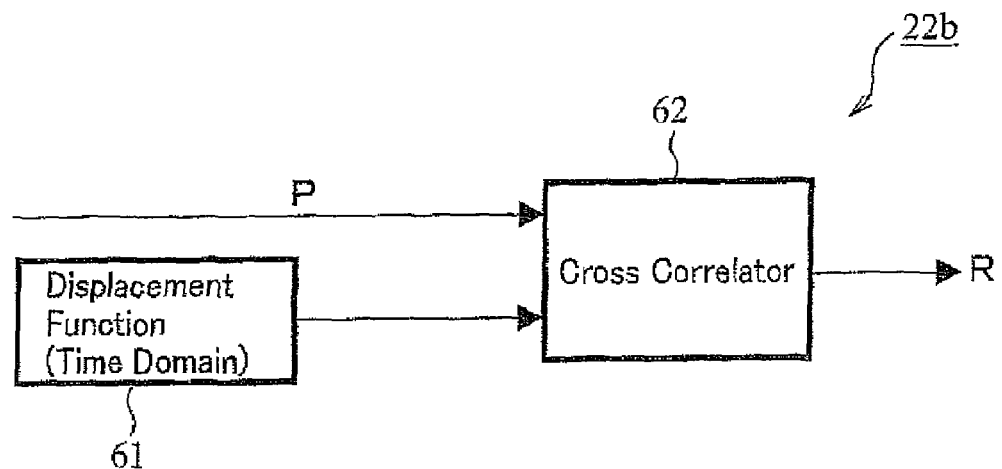
FIGS. 9A and 9B are configuration drawings of expansion detectors of a second embodiment of the present invention, respectively.
Figure 9B:
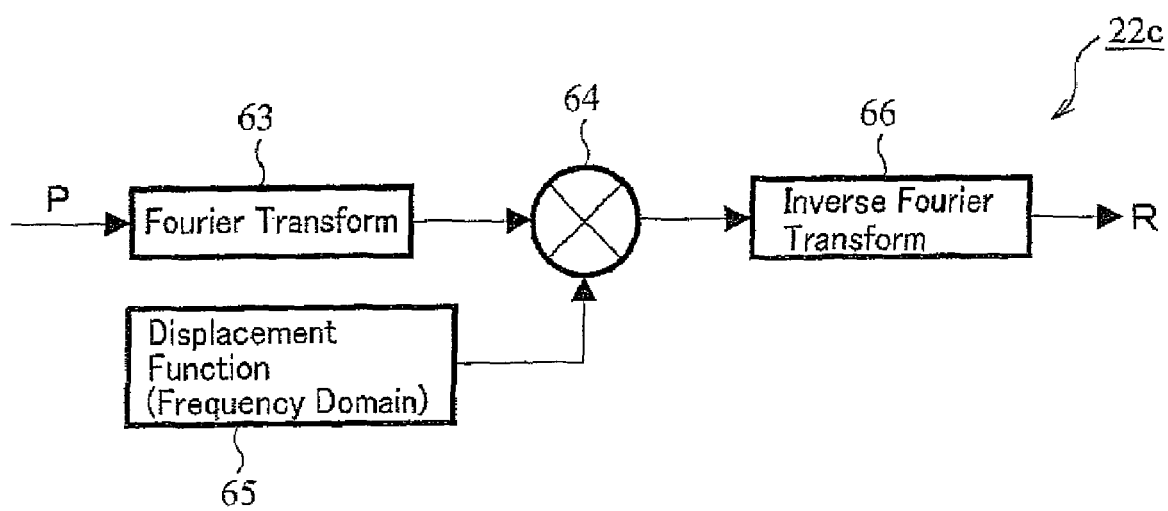

FIGS. 9A and 9B are configuration drawings of the expansion detector 22 for performing a cross correlation with a template; FIG. 9A shows an configuration of an expansion detector 22b for performing a cross correlation in a time domain; and FIG. 9B shows an configuration of an expansion detector 22c for performing a cross correlation in a frequency domain.

By a cross correlator 62, the expansion detector 22b performs in the time domain a cross correlation between the displacement signal P from the cross correlator 30 and a displacement function 61, where a displacement form characteristic of a tissue expansion is memorized as a function in a memory; and outputs the tissue expansion component R to the scan converter 23.

Figure 10:
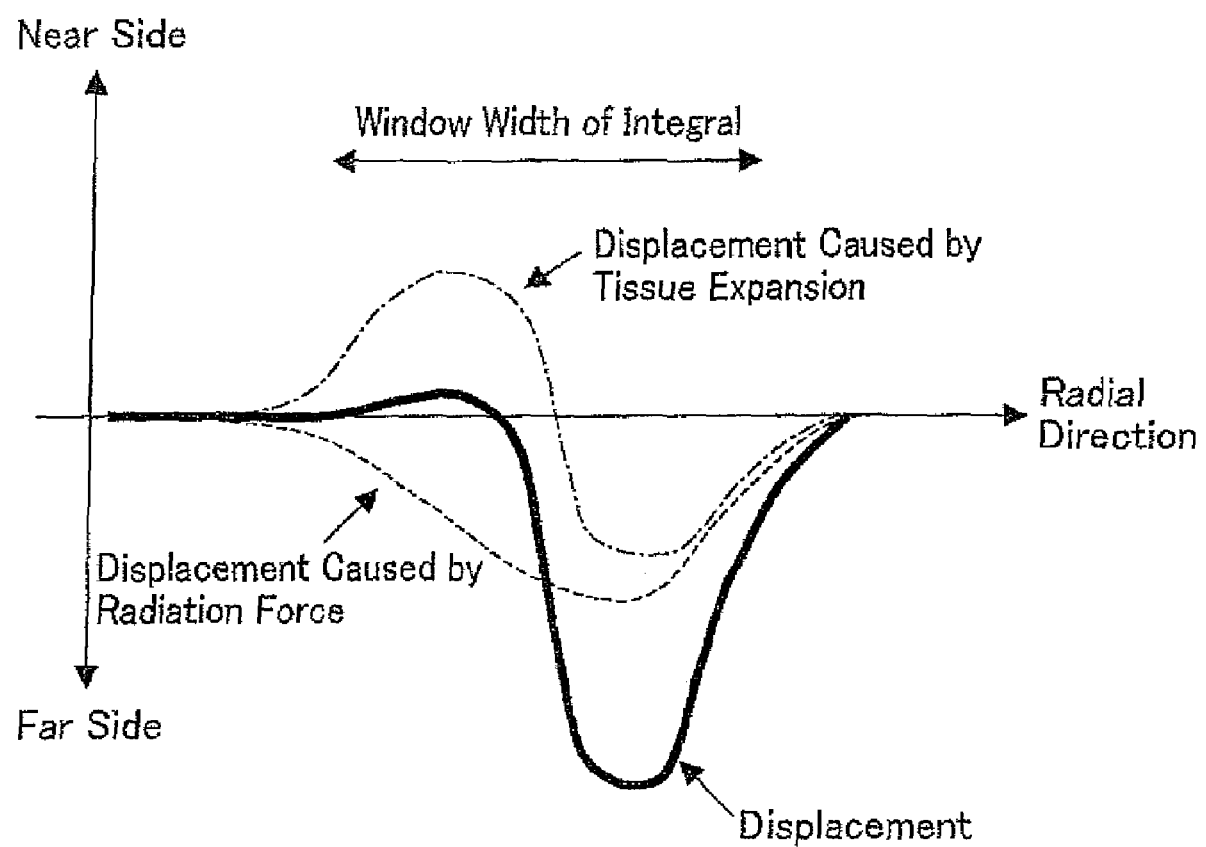
FIG. 10 is a drawing explaining an integral window.

Also in the configuration of the first embodiment, when a tissue motion and a space frequency are largely different like a local tissue expansion, it is possible to make the configuration a spatial low-pass filter at an integral window approximately equal to a displacement width caused by a tissue expansion. A dashed line of FIG. 10 indicates a displacement caused by a tissue expansion, and a broken line indicates a displacement caused by a radiation force. A displacement is not caused at the center point of the tissue expansion: the depth of a place is shallower, the place displaces so as to become nearer to a body surface; and a depth of a place is deeper, the place displaces so as to become farther from the body surface. On one hand, depending on a radiation force if any, a displacement is totally caused at a place far from the body surface. A solid line is a resultant displacement of these displacements: at a shallow place in depth, a displacement caused by the tissue expansion and that caused by the radiation force overlap with each other; and at a deep place in depth, a displacement caused by the tissue expansion and that caused by the radiation force overlap each other. Using this phenomenon, if a filtering processing is performed by setting an integral window of a width of a displacement due to a tissue expansion by the setting 54 of an integral window (see FIG. 3), and integrating the integral window by the integrator 52, it is possible to distinguish between the tissue expansion and the tissue motion. However, with respect to the distinction between the radiation force and the tissue expansion, a spatial frequency is not always largely different.

Figure 11A:
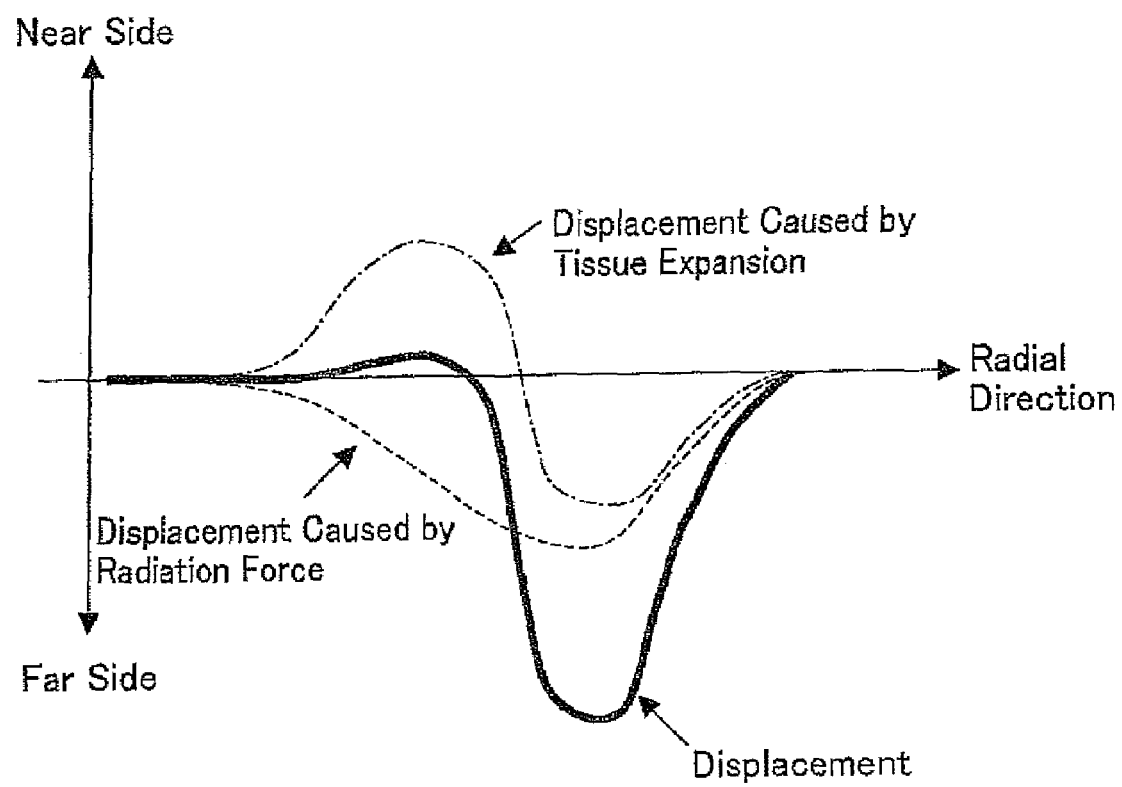
FIGS. 11A and 11B are drawings explaining a method of using a template and detecting a tissue expansion.
Figure 11B:
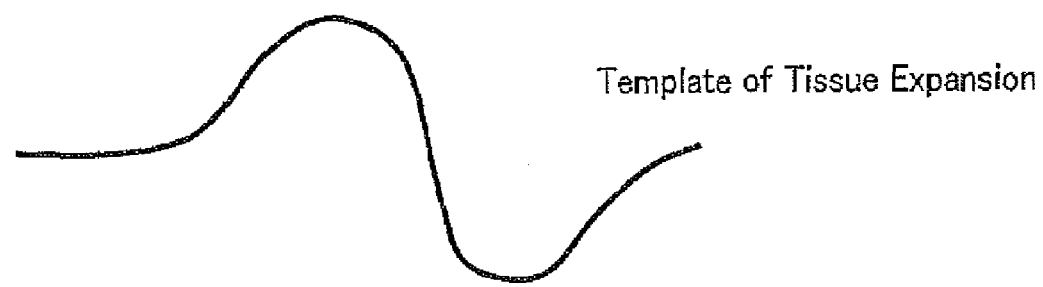

In this case a method of the embodiment is useful. According to the method, a waveform (displacement caused by a tissue expansion described in FIG. 11A) presumed in advance, as shown in FIG. 11B, as a spatial distribution form of a displacement is memorized in a memory as a displacement function 61, and by taking a cross correlation between the waveform and the tissue expansion, only a displacement peculiar to the tissue expansion is extracted. In addition, if a tissue motion is once removed according to the method and then a patter matching is performed, it is more effective. Although the pattern matching may be a one-dimensional displacement function, it is possible to widen an application range of the embodiment by making the pattern matching a two-dimensional displacement function when the transmit directions of the therapeutic ultrasound beam and the imaging ultrasound beam do not always match.

Furthermore, it is also possible to once perform a fast Fourier transform and change a signal to a frequency domain, to extract a component corresponding to a spatial frequency of a template, to return the component to a time domain by an inverse Fourier transform, and to image the component. Although mathematically an equivalent processing to the pattern matching, this has an advantage of high speed capability in such a case of a processor being used where the fast Fourier transform is mounted.

Specifically, with respect to the expansion detector 22c in FIG. 9B, a Fourier transform 63 transforms the displacement signal P of the time domain to the frequency domain, a multiplier 64 multiplies this transformed signal by a displacement function 65 where a displacement form transformed into the frequency domain is memorized as a function in a memory, and an inverse Fourier transform 66 outputs the tissue expansion component R, which is transformed into the time domain, to the scan converter 23.

In addition, there are also effective methods: a method of having a few kinds of template forms in any one of the time domain and the frequency domain and using a result of which detection sensitivity is highest; and a method of performing a weighted averaging of a plurality of template matching results and enhancing a robustness of the result.

Third Embodiment

In the embodiments, although the methods of distinguishing the radiation force and the tissue expansion in a signal processing unit are described, it is also possible to suppress a displacement caused by the radiation force and to stand out a displacement caused by the tissue expansion depending on a treatment method if any.

Figure 12:
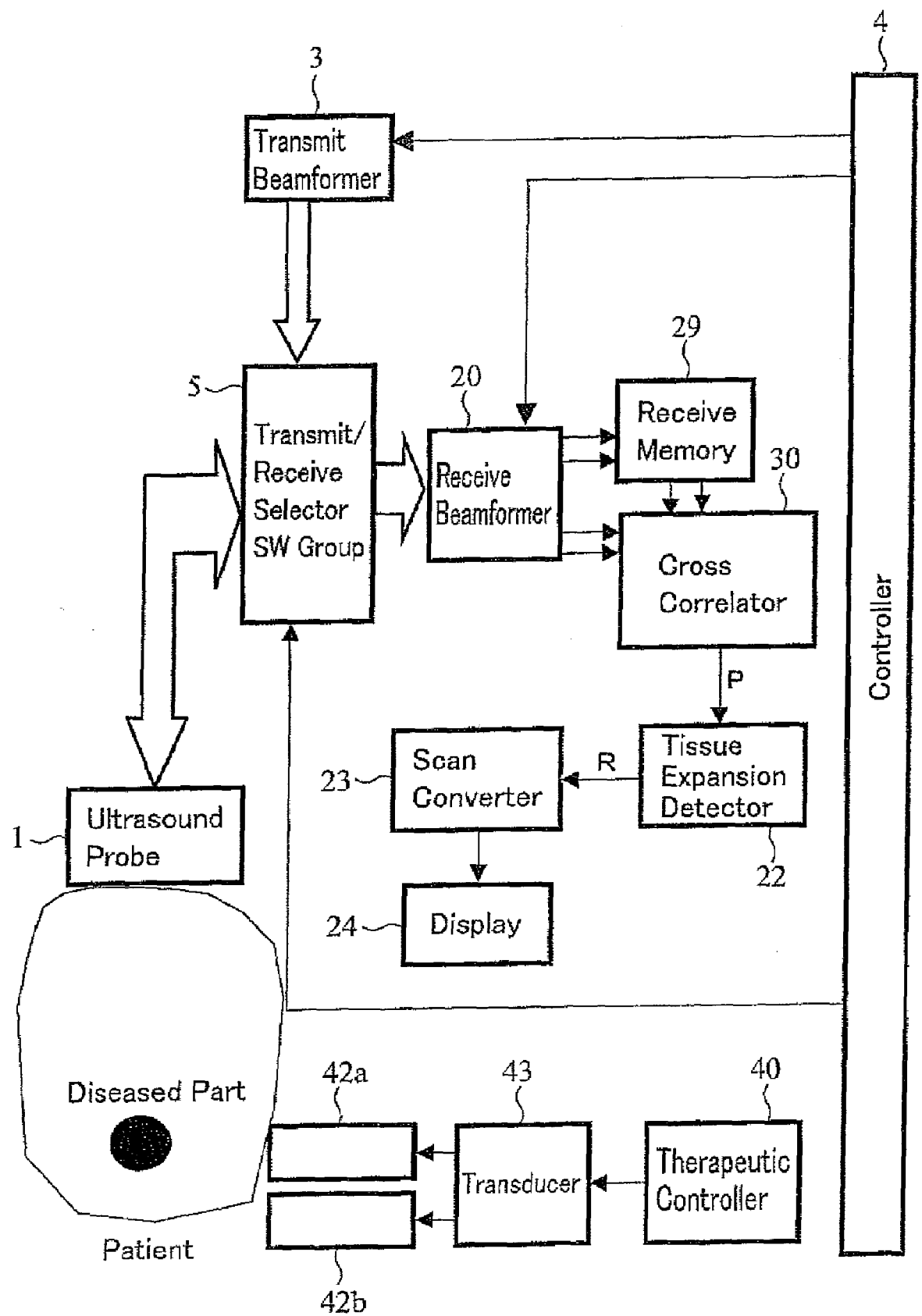
FIG. 12 is a configuration drawing of an expansion detector of a third embodiment of the present invention.

In FIG. 12 is shown a configuration drawing of an ultrasound diagnosis apparatus of a third embodiment. To the same elements as in FIG. 1 are appended the same symbols; descriptions thereof will be omitted and only different points thereof will be described.

In the embodiment the therapeutic device 41 of a transmit transducer is divided into two piezoelectric devices 42a, 42b, and a transmitter 43 uses a signal from the therapeutic controller 40 and drives the devices 42a, 42b.

Figure 13:
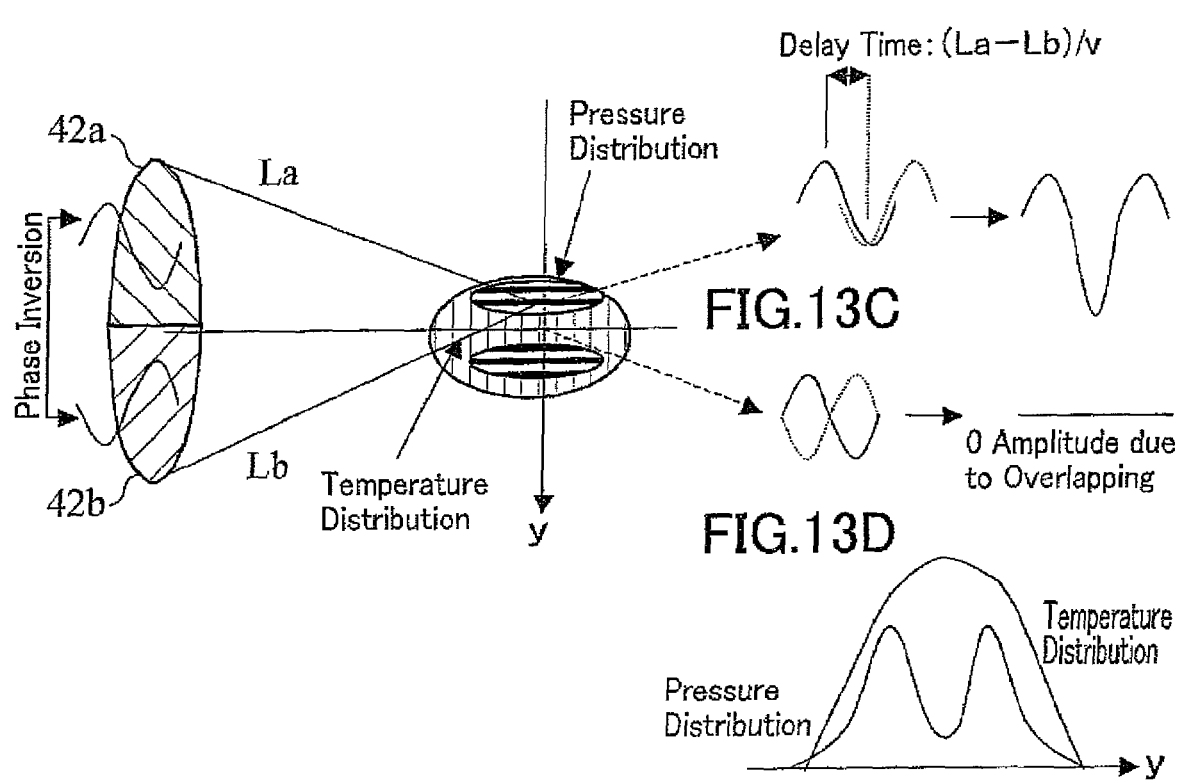
FIGS. 13A, 13B, 13C, and 13D are drawings explaining a split focus.

As shown in FIG. 13A, each of the piezoelectric devices 42a, 42b mutually inverts therapeutic ultrasound beams like semicircles in their phases, and converges and radiates the beams on a same focus. Thus although on a radiation axis ultrasound intensities overlap with each other (see FIG. 13C), in FIG. 13A a delay time (La–Lb/v) by a distance difference (La–Lb) between each transducer element configuring the piezoelectric devices 42a, 42b and the radiation axis, and the phases of the beams strengthen each other (see FIG. 13B). Namely, in an example where the therapeutic device 41 is divided into two, there exist two pressure maximum points (see FIG. 13A). If a heating coagulation therapy is performed by using this sound field, a temperature rise becomes maximum at a place surrounded by a plurality of pressure peaks due to a thermal conduction (see FIG. 13D). Therefore, because the place of the maximum temperature rise and that of the maximum pressure are displaced, an effect of the radiation force is largely reduced and only that of the tissue expansion is highlighted. This method is called split focus.

In other words, the piezoelectric devices 42a, 42b are configured to consist of a plurality of transducers for converging and radiating therapeutic ultrasound beams on a focus, to be two-dimensionally divided into a plurality of areas through a line passing through an radiation axis passing the focus, and so that phases of the therapeutic ultrasound beams converged and radiated from neighboring areas are phase-inverted with each other.

Fourth Embodiment

In each of the embodiments, a tissue expansion caused by a temperature rise and that caused by a thermal denaturation of a protein are explained without a distinction. But, in performing an actual therapy, it is extremely important to distinguish a change between an irreversible change such as a thermal denaturation and a reversible change such as a thermal change. The temperature rise only is not sufficient as an index of a therapeutic effect. It is because it not possible to determine whether a therapy is completed with respect to each tissue because of a motion of a living body if how long a time has elapsed at what temperature is not known. On one hand, the thermal denaturation is decided by a temperature and a time elapse thereof, and therefore, completely corresponds one to one to whether or not the therapy is completed.

Figure 14:
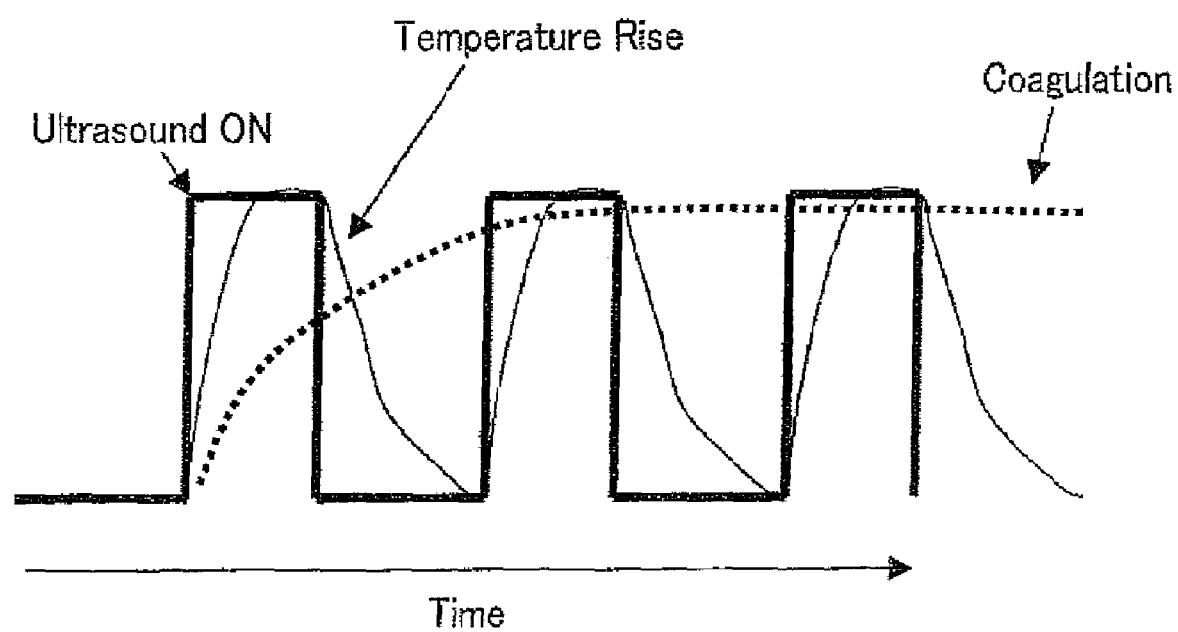
FIG. 14 is a drawing explaining a case of repeating a radiation and stop of an ultrasound.

Consequently, as shown in FIG. 14, if ON and OFF of any one of an ultrasound radiation and an RF therapy are repeated, a temperature repeats rise and fall; however, a thermal denaturation amount only increases monotonously, a thermal denaturation is caused even during when the therapy is made OFF. By using a time when a selection ratio of the temperature rise to the thermal denaturation, and by detecting the tissue expansion, it is possible to separate the effect of the temperature rise from that of the thermal denaturation. Namely, after a therapeutic ultrasound beam is radiated, a pause of the radiation taken for a period, and a tissue expansion (volume change) of the pause period is detected.

Modification Example

The present invention is not limited to the embodiments, and for example, various modifications are possible as below.

(1) Although each of the embodiments uses a therapeutic ultrasound beam generated by the therapeutic device 41 or the piezoelectric devices 42a, 42b, it is possible to use a converging ultrasound beam generated by the ultrasound probe 1, and also to converge and radiate an RF electromagnetic wave.

What is claimed is:

1. An ultrasound diagnosis apparatus having an ultrasound probe in which a plurality of transducer elements are arrayed, and which converges and radiates an ultrasound on a patient and detects a reflection wave thereof; and imaging a tomogram of the patient, using the reflection wave, the apparatus comprising:
a cross correlator for performing a pattern matching between the tomogram imaged with one frame and the tomogram imaged with another frame and operating a displacement signal, the pattern matching being performed by taking a cross correlation through application of a first displacement function for expressing a displacement such that a place becomes closer to a body surface at a shallow depth and a displacement such that a place becomes farther from the body surface at a greater depth; and
a tissue expansion detector for performing a second pattern matching between the displacement signal and a second displacement function for expressing a displacement form caused by a partial tissue expansion of the patient, wherein a tissue expansion generated at a part of the patient is extracted from the second pattern matching.

2. The ultrasound diagnosis apparatus according to claim 1, wherein any of the pattern matching, the second pattern matching, and the both is performed by using the cross correlation.

3. The ultrasound diagnosis apparatus according to claim 1, wherein after a filtering processing of setting and integrating an integral window at a boundary between a variation caused by a tissue motion of the patient and a variation caused by the tissue expansion is performed for the displacement signal, an extraction of the tissue expansion is performed.

4. An ultrasound diagnosis apparatus having an ultrasound probe in which a plurality of transducer elements are arrayed, and which converges and radiates an ultrasound on a patient and detects a reflection wave thereof; and imaging a tomogram of the patient, using the reflection wave, the apparatus comprising:
a cross correlator for performing a pattern matching between the tomogram imaged with one frame and the tomogram imaged with another frame and operating a displacement signal, the pattern matching being performed by taking a cross correlation through application of a first displacement function for expressing a displacement such that a place becomes closer to a body surface at a shallow depth and a displacement such that a place becomes farther from the body surface at a greater depth;
a Fourier transform for transforming the displacement signal into a frequency domain;
a multiplier for multiplying the displacement signal transformed into the frequency domain by a second displacement function for expressing a displacement form caused by a partial tissue expansion of the patient in the frequency domain; and
an inverse Fourier transform for inverse transforming the signal of the frequency domain multiplied by the multiplier into a time domain,
wherein the tissue expansion is extracted by using the time domain signal inverse transformed.

5. The ultrasound diagnosis apparatus according to claim 4, wherein after a filtering processing of setting and integrating an integral window at a boundary between a variation caused by a tissue motion of the patient and a variation caused by the tissue expansion is performed for the displacement signal, an extraction of the tissue expansion is performed.

6. An ultrasound diagnosis apparatus having an ultrasound probe in which a plurality of transducer elements are arrayed, and which converges and radiates an ultrasound on a patient and detects a reflection wave thereof; and imaging a tomogram of the patient, using the reflection wave, wherein a tissue expansion is generated by converging and radiating a therapeutic converging beam, which is any one of the ultrasound, a second ultrasound, an electromagnetic wave, and a combination of these, on a part of the patient, the apparatus comprising:
a cross correlator for performing a pattern matching between the tomogram imaged with a frame and the tomogram imaged with another frame and operating a displacement signal by using a cross correlation, the pattern matching being performed by taking the cross correlation through application of a displacement function for expressing a displacement such that a place becomes closer to a body surface at a shallow depth and a displacement such that a place becomes farther from the body surface at a greater depth;

a radial component calculator for calculating a radial component of the therapeutic converging beam;

an integrator for integrating the radial component and calculating an integral amount thereof; and a subtracter for operating a difference between the radial component and the integral amount, wherein the tissue expansion is extracted by using the difference.

7. The ultrasound diagnosis apparatus according to claim 6, wherein the pattern matching is performed for a temporal change of a plurality of imaging signals by using the tomograms of not less than three frames, and the temporal change is used.

8. The ultrasound diagnosis apparatus according to claim 6 comprising a controller configured to stop a radiation of the therapeutic converging beam when the tissue expansion is detected by not less than a predetermined amount.

9. The ultrasound diagnosis apparatus according to claim 6, wherein after the therapeutic converging beam is radiated, a pause of the radiation is taken for a period, and the tissue expansion of the pause period is detected.

10. The ultrasound diagnosis apparatus according to claim 6, wherein the therapeutic converging beam is a therapeutic ultrasound beam of any of the ultrasound, the second ultrasound, and both, and wherein the therapeutic ultrasound beam is converged and radiated so that a plurality of pressure maximum values is formed in a vertical plane with respect to a radial direction.

11. The ultrasound diagnosis apparatus according to claim 6, wherein the therapeutic converging beam is a therapeutic ultrasound beam of any of the ultrasound, the second ultrasound, and the both, and wherein a plurality of transducers configured to converge and radiate therapeutic ultrasound beams on a focus are two-dimensionally divided into a plurality of areas through a line passing through a radiation axis passing the focus, and phases of the therapeutic ultrasound beams converged and radiated from the areas which neighbor are inverted with each other.

12. An ultrasound diagnosis apparatus having an ultrasound probe in which a plurality of transducer elements are arrayed, and which converges and radiates an ultrasound on a patient and detects a reflection wave thereof; and imaging a tomogram of the patient, using the reflection wave, the apparatus comprising:

a cross correlator for performing a pattern matching between the tomogram imaged with one frame and the tomogram imaged with another frame and operating a displacement signal, the pattern matching being performed by taking a cross correlation through application of a first displacement function for expressing a displacement such that a place becomes closer to a body surface at a shallow depth and a displacement such that a place becomes farther from the body surface at a greater depth; and a tissue expansion detector for performing a second pattern matching between the displacement signal and a second displacement function for expressing a displacement form caused by a partial tissue expansion of the patient, wherein the tissue expansion detector detects a volume change generated at a part of the patient for a pause period of a radiation of the ultrasound by the ultrasound probe.

\* \* \* \* \*